United States Patent
Moon

(10) Patent No.: US 11,564,848 B2
(45) Date of Patent: Jan. 31, 2023

(54) METHOD OF PRODUCING A CUSTOM-FIT ORTHOPEDIC IMMOBILIZATION DEVICE

(71) Applicant: Alex Moon, Las Cruces, NM (US)

(72) Inventor: Alex Moon, Las Cruces, NM (US)

(73) Assignee: EXOSSEUS LLC, Las Cruces, NM (US)

(*) Notice: Subject to any disclaimer, the term of this patent is extended or adjusted under 35 U.S.C. 154(b) by 584 days.

(21) Appl. No.: 16/586,780

(22) Filed: Sep. 27, 2019

(65) Prior Publication Data

US 2020/0100947 A1  Apr. 2, 2020

Related U.S. Application Data

(60) Provisional application No. 62/737,208, filed on Sep. 27, 2018.

(51) Int. Cl.

| | | |
|---|---|---|
| *A61F 13/06* | (2006.01) | |
| *G06T 7/62* | (2017.01) | |
| *G06T 7/00* | (2017.01) | |
| *G16H 30/20* | (2018.01) | |
| *A61B 6/00* | (2006.01) | |
| *A61N 1/36* | (2006.01) | |
| *A61F 13/10* | (2006.01) | |

(Continued)

(52) U.S. Cl.
CPC ............... *A61F 13/06* (2013.01); *A61B 6/505* (2013.01); *A61F 13/10* (2013.01); *A61F 13/104* (2013.01); *A61F 13/107* (2013.01); *A61N 1/36014* (2013.01); *B33Y 10/00* (2014.12); *B33Y 50/00* (2014.12); *B33Y 80/00* (2014.12); *G06T 7/0012* (2013.01); *G06T 7/62* (2017.01); *G16H 30/20* (2018.01); *A61F 2013/00629* (2013.01); *G06T 2207/10116* (2013.01)

(58) Field of Classification Search
None
See application file for complete search history.

(56) References Cited

U.S. PATENT DOCUMENTS

| | | |
|---|---|---|
| 8,430,829 B1 | 4/2013 | Marchetti |
| 8,613,716 B2 | 12/2013 | Summit et al. |

(Continued)

FOREIGN PATENT DOCUMENTS

| | | |
|---|---|---|
| EP | 2585007 B1 | 5/2013 |
| EP | 3315098 A1 | 5/2018 |

(Continued)

OTHER PUBLICATIONS

Caruso, Catherine, "You can Get a 3-D-Printed Case for a Broken Bone", MIT Technology Review, https://www.technologyreview.com/s/601931/you-can-get-a-3-d-printed-case-for-a-broken-bone/, 8 pages, Jul. 25, 2016.

(Continued)

*Primary Examiner* — Mohammad M Ameen
(74) *Attorney, Agent, or Firm* — Loza & Loza LLP; Kevin L. Soules

(57) ABSTRACT

A method and system for creating a custom-fit orthopedic cast comprises obtaining at least one measurements taken from at least one image of a body part, selecting a template cast, modifying the template cast according to the measurements taken from the at least one image to generate a custom cast model and rendering a custom cast based on the custom cast model.

15 Claims, 10 Drawing Sheets

(51) Int. Cl.
　　　*B33Y 10/00*　　(2015.01)
　　　*B33Y 50/00*　　(2015.01)
　　　*B33Y 80/00*　　(2015.01)
　　　*A61F 13/00*　　(2006.01)

(56) References Cited

U.S. PATENT DOCUMENTS

| | | | |
|---|---|---|---|
| 8,775,133 | B2 | 7/2014 | Schroeder |
| 8,781,557 | B2 | 7/2014 | Dean et al. |
| 9,839,549 | B2 | 12/2017 | Walborn et al. |
| 9,972,406 | B2 | 5/2018 | Lin et al. |
| 2005/0238133 | A1 | 10/2005 | Koppe et al. |
| 2007/0027667 | A1* | 2/2007 | Osborn ............ G16H 50/50 703/11 |
| 2009/0306714 | A1 | 12/2009 | Crompton |
| 2014/0017651 | A1* | 1/2014 | Sugimoto ........... B29C 64/112 264/401 |
| 2014/0330183 | A1* | 11/2014 | Kazemtabrizi ...... A61F 5/0118 602/12 |
| 2015/0237327 | A1 | 8/2015 | Rustici et al. |
| 2015/0283287 | A1* | 10/2015 | Agarwal .............. A61L 15/46 424/650 |
| 2015/0328016 | A1* | 11/2015 | Summit .............. A61F 5/0123 703/1 |
| 2016/0074203 | A1 | 3/2016 | Hall |
| 2016/0213320 | A1* | 7/2016 | Shabah ............... A61N 1/0484 |
| 2016/0339607 | A1 | 11/2016 | Muñoz et al. |
| 2017/0079830 | A1 | 3/2017 | Chhatrala et al. |
| 2017/0216078 | A1 | 8/2017 | Rivlin et al. |
| 2017/0241919 | A1 | 8/2017 | Machii et al. |
| 2018/0001547 | A1 | 1/2018 | Cuypers et al. |

FOREIGN PATENT DOCUMENTS

| | | |
|---|---|---|
| WO | 2010054341 A1 | 5/2010 |
| WO | 2016142319 A1 | 9/2016 |

OTHER PUBLICATIONS

"Mediprint"; Mediprint; Website [online], 2019 [retrieved Sep. 26, 2019]. Retrieved from the internet: <https://mediprint.us/>.

Fitzpatrick, Angus P. et al. "Design of a Patient Specific, 3D printed Arm Cast"; DesTEch Conference Proceedings, The International Conference on Design and Technology, vol. 2017, https://www.knepublishing.com/index.php/KnE-Engineering/article/view/607/1895, 8 pages (2017).

"Activearmor"; Activearmor; Website [online], 2019 [retrieved Sep. 26, 2019]. Retrieved from the internet: <https://activearmor.com>, 7 pages.

"Evilldesign", Website [online], 2019 [retrieved Sep. 26, 2019]. Retrieved from the internet: <http://www.evilldesign.com/cortex>, 12 pages.

"Braceworks"; Braceworks; Website [online]. 2019 [retrieved Sep. 26, 2019], Retrieved from the internet: <https://braceworks.ca/2016/04/16/health-tech/could-the-3d-printed-cast-put-plaster-to-pasture/>.

Sciencedaily, Science News, "Swapping plaster casts for 3D printing", https://www.sciencedaily.com/releases/2016/04/160414145348.htm, 4 pages, Apr. 14, 2016.

"Mediprint"; Mediprint; Website [online], 2019 [retrieved Sep. 26, 2019]. Retrieved from the internet: <hhttp://mediprint3d.com.mx/>.

* cited by examiner

METHOD OF PRODUCING A CUSTOM-FIT ORTHOPEDIC IMMOBILIZATION DEVICE

CROSS REFERENCE TO RELATED PATENT APPLICATIONS

This patent application claims the priority and benefit under 35 U.S.C. § 119(e) of U.S. Provisional Patent Application Ser. No. 62/737,208, filed Sep. 27, 2018, entitled "METHOD OF PRODUCING A CUSTOM-FIT ORTHOPEDIC IMMOBILIZATION DEVICE." U.S. Provisional Patent Application Ser. No. 62/737,208 is herein incorporated by reference in its entirety.

TECHNICAL FIELD

Embodiments are generally related to orthopedic immobilization devices. Embodiments are additionally related to custom fit casts for injured limbs. Embodiments are also related to a methods and systems for producing custom-fit casts for injured limbs.

BACKGROUND

Estimates show 6-6.5 million people in the United States annually are in need of a cast for injured limbs. Current casting systems ("traditional casts/casting systems") are made of plaster of Paris or fiberglass and have been around for over 160 years and 50 years, respectively. They are bulky, uncomfortable, unhygienic, and archaic.

Most broken bones and other limb injuries are casted for support during the healing process. The cast immobilizes the limb to allow the bone fracture to heal itself in proper position. Casts must be worn for a period of time which can span from several days to several months, depending on the severity of the injury. Problems with rigid casts and splints include inconsistent construction, limitations in customized sizing of the rigid cast or splint to a specific patient's anatomy, irritability to the patient's skin, limited waterproof or water resistant options, and limited breathability.

Traditional casts are heavy, uncomfortable, and subject to molding and degradation by water and sweat. Mildew and bacteria thrive in such an environment and can create an unpleasant odor. When a patient wears a cast or splint, the size of their limb may change due to atrophy, swelling, or reduced swelling. The patient's limb may also change due to healing of the skin around the injury, or as the result of being enclosed in a traditional cast or splint for extended periods of time.

The cast usually comprises of layers of fabric, cotton padding tape wrapped around the limb, and plaster of Paris or fiberglass. The fiberglass cast is lighter, somewhat air permeable, and more durable than the plaster cast. However, the fabric and cotton padding against the skin underneath a fiberglass cast may become wet, just as in the plaster cast. Imperfect application of a cast can result in multiple complications including skin breakdown, discomfort, emergency room visits, compartment syndromes, loss of fixation or fracture reduction, need for surgical intervention, nerve injury, and vascular injury.

Current solutions for custom cast manufacturing are insufficient. Certain solutions require scanning with custom equipment and then outsourcing cast manufacturing, causing unnecessary delays.

It would be advantageous to design, produce and deploy a custom-fit cast that overcomes the deficiencies of conventional casts. Accordingly, the methods and systems disclosed herein are intended to address these issues, by introducing new methods and systems for creating custom-fit casts as disclosed herein.

SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, an aspect of the disclosed embodiments to provide orthopedic immobilization devices.

In addition, it is another aspect of the embodiments to provide custom-fit casts for injured limbs.

It is, therefore, another aspect of the disclosed embodiments to provide methods for producing custom fit casts for injured limbs.

The aforementioned aspects and other objectives and advantages can now be achieved as described herein.

In an exemplary embodiment a patient X-ray can be taken and the radiology file can be uploaded to an image processing system. Computer imaging software can be used to accurately measure, to less than a millimeter, the dimensions of the patient's injury. Each dimension is entered into a design software program which can be used to change the dimensions of a preset model cast. A customized CAD model of the custom-fit cast is then sent to a 3D printer, where the cast is precision printed.

A system and method for creating an orthopedic cast, can therefore comprise obtaining at least one measurements taken from at least one image of a body part, selecting a template cast, modifying the template cast according to the measurements taken from the at least one image to generate a custom cast model and rendering a custom cast based on the custom cast model.

In another embodiment, a system comprises an imaging device configured to take at least one image of at least one anatomical structure, an image processing system comprising at least one processor and a storage device communicatively coupled to the at least one processor, the storage device storing instructions which, when executed by the at least one processor, cause the at least one processor to perform operations comprising: extracting dimensions of the at least one anatomical structure in the at least one image taken by the imaging device, selecting a template cast model, and modifying the template cast model according to the measurements taken from the at least one image to generate a custom cast model, and a 3D printing device configured to render a custom cast according to the custom cast model.

In an embodiment the imaging device comprises an X-ray. In an embodiment the X-ray is provided to the at least one image processing system as a DICOM file. In an embodiment the image processing system is further configured to perform operations comprising determining a number of pixels that defines the at least one anatomical structure, reading the length per pixel value associated with the DICOM file and assigning the dimension of the at least one anatomical structure according to the length per pixel value associated with the DICOM file and the number of pixels that defines the at least one anatomical structure.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

Figure 1:
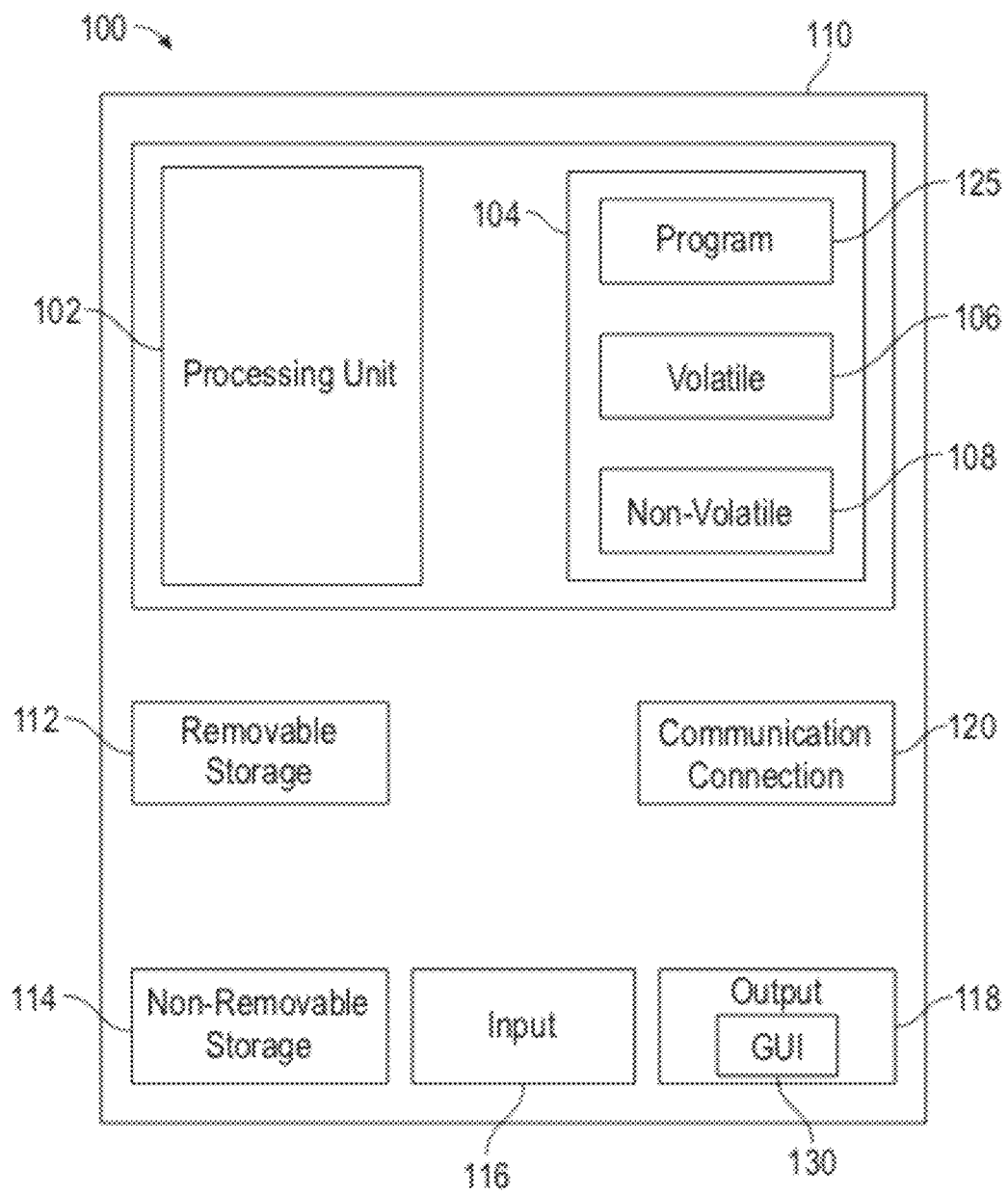
FIG. 1 depicts a block diagram of a computer system which is implemented in accordance with the disclosed embodiments.

The particular values and configurations discussed in the following non-limiting examples can be varied, and are cited merely to illustrate one or more embodiments and are not intended to limit the scope thereof.

Example embodiments will now be described more fully hereinafter with reference to the accompanying drawings, in which illustrative embodiments are shown. The embodiments disclosed herein can be embodied in many different forms and should not be construed as limited to the embodiments set forth herein; rather, these embodiments are provided so that this disclosure will be thorough and complete, and will fully convey the scope of the embodiments to those skilled in the art. Like numbers refer to like elements throughout.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. In addition, the term "based on" may be understood as not necessarily intended to convey an exclusive set of factors and may, instead, allow for existence of additional factors not necessarily expressly described, again, depending at least in part on context.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
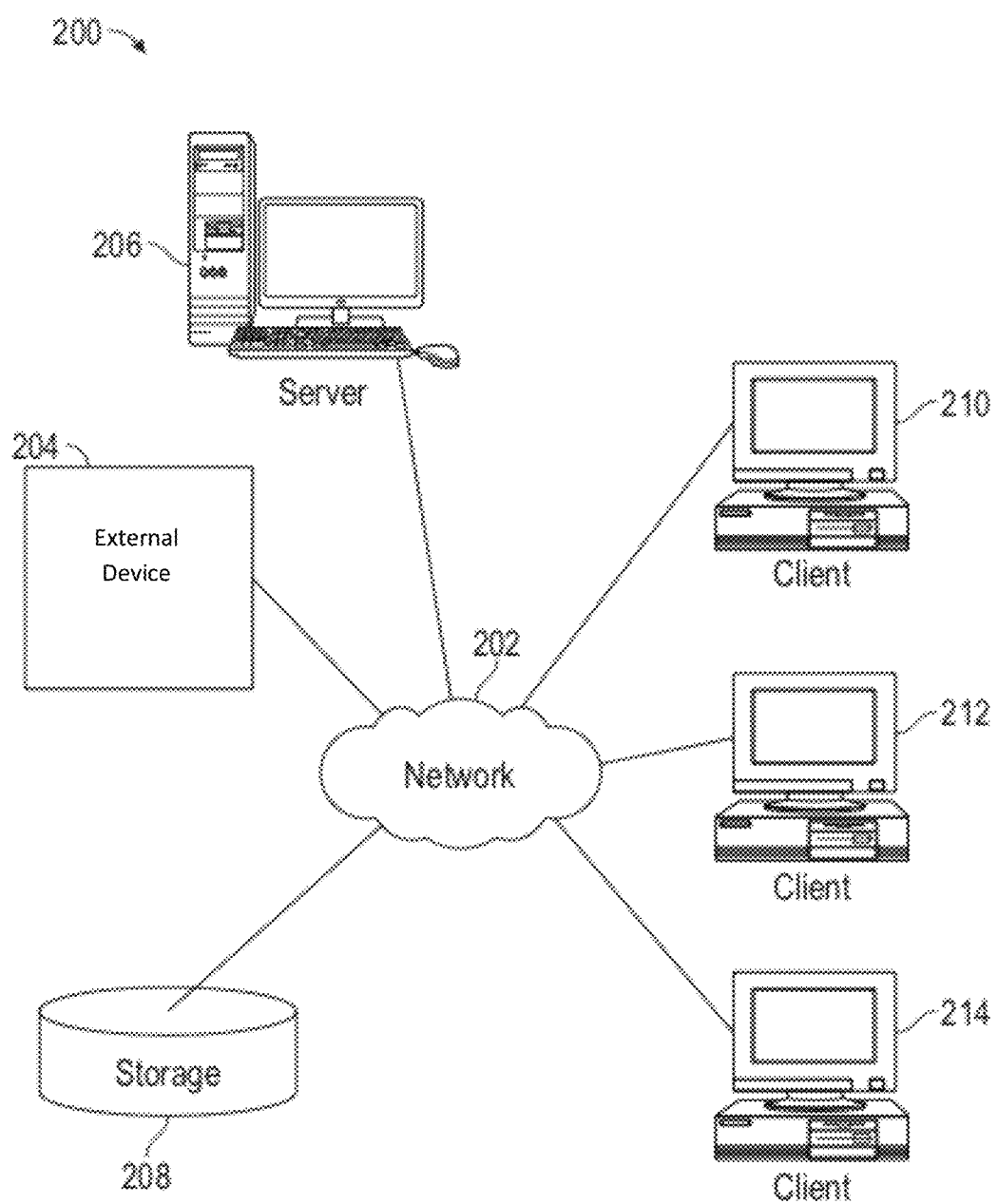
FIG. 2 depicts a graphical representation of a network of data-processing devices in which aspects of the present embodiments may be implemented.
Figure 3:
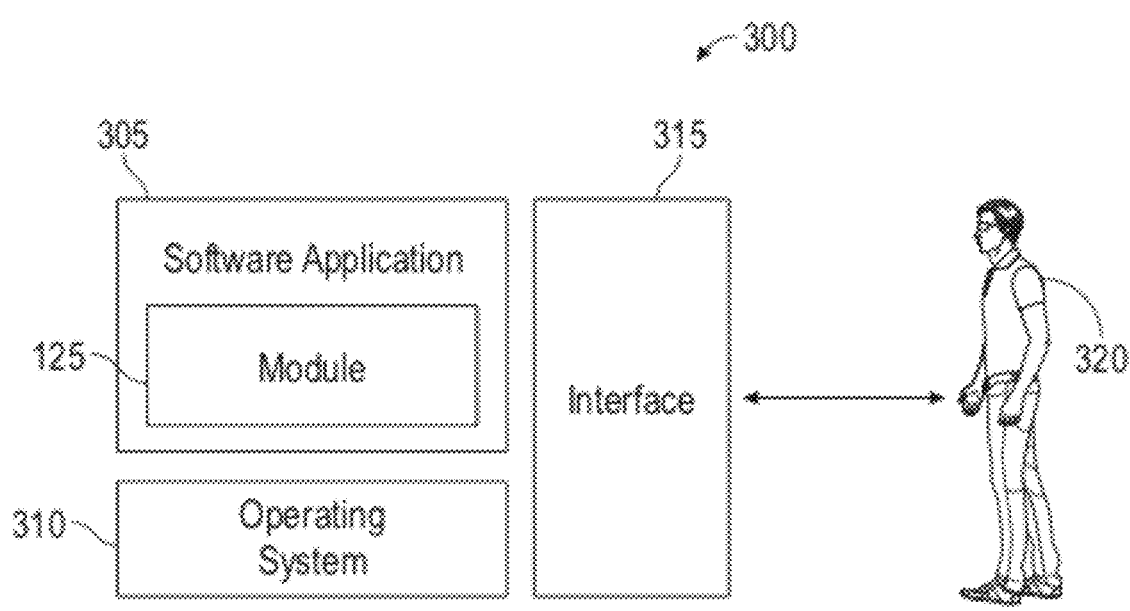
FIG. 3 depicts a computer software system for directing the operation of the data-processing system depicted in FIG. 1, in accordance with an embodiment.

FIGS. 1-3 are provided as exemplary diagrams of data-processing environments in which embodiments disclosed herein may be implemented. It should be appreciated that FIGS. 1-3 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

A block diagram of a computer system 100 that executes programming for implementing parts of the methods and systems disclosed herein is shown in FIG. 1. A computing device in the form of a computer 110 configured to interface with sensors, peripheral devices, and other elements disclosed herein may include one or more processing units 102, memory 104, removable storage 112, and non-removable storage 114. Memory 104 may include volatile memory 106 and non-volatile memory 108. Computer 110 may include or have access to a computing environment that includes a variety of transitory and non-transitory computer-readable media such as volatile memory 106 and non-volatile memory 108, removable storage 112 and non-removable storage 114. Computer storage includes, for example, random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage, or other magnetic storage devices, or any other medium capable of storing computer-readable instructions as well as data including image data.

Computer 110 may include or have access to a computing environment that includes input 116, output 118, and a communication connection 120. The computer may operate in a networked environment using a communication connection 120 to connect to one or more remote computers, remote sensors, detection devices, hand-held devices, multifunction devices (MFDs), mobile devices, tablet devices, mobile phones, Smartphones, or other such devices. The remote computer may also include a personal computer (PC), server, router, network PC, RFID enabled device, a peer device or other common network node, or the like. The communication connection may include a Local Area Network (LAN), a Wide Area Network (WAN), Bluetooth connection, or other networks. This functionality is described more fully in the description associated with FIG. 2 below.

Output 118 is most commonly provided as a computer monitor, but may include any output device. Output 118 and/or input 116 may include a data collection apparatus associated with computer system 100. In addition, input 116, which commonly includes a computer keyboard and/or pointing device such as a computer mouse, computer track pad, or the like, allows a user to select and instruct computer system 100. A user interface can be provided using output 118 and input 116. Output 118 may function as a display for displaying data and information for a user, and for interactively displaying a graphical user interface (GUI) 130.

Note that the term "GUI" generally refers to a type of environment that represents programs, files, options, and so forth by means of graphically displayed icons, menus, and dialog boxes on a computer monitor screen. A user can interact with the GUI to select and activate such options by directly touching the screen and/or pointing and clicking with a user input device 116 such as, for example, a pointing device such as a mouse and/or with a keyboard. A particular item can function in the same manner to the user in all applications because the GUI provides standard software routines (e.g., module 125) to handle these elements and report the user's actions. The GUI can further be used to display the electronic service image frames as discussed below.

Computer-readable instructions, for example, program module or node 125, which can be representative of other modules or nodes described herein, are stored on a computer-readable medium and are executable by the processing unit 102 of computer 110. Program module or node 125 may include a computer application. A hard drive, CD-ROM, RAM, Flash Memory, and a USB drive are just some examples of articles including a computer-readable medium.

FIG. 2 depicts a graphical representation of a network of data-processing systems 200 in which aspects of the present embodiments may be implemented. Network data-processing system 200 is a network of computers or other such devices such as mobile phones, smartphones, sensors, detection devices, controllers and the like in which embodiments may be implemented. Note that the system 200 can be implemented in the context of a software module such as program module 125. The system 200 includes a network 202 in communication with one or more clients 210, 212, and 214. Network 202 may also be in communication with one or more device 204, servers 206, and storage 208. Network 202 is a medium that can be used to provide communications links between various devices and computers connected together within a networked data processing system such as computer system 100. Network 202 may include connections such as wired communication links, wireless communication links of various types, fiber optic cables, quantum, or quantum encryption, or quantum teleportation networks, etc. Network 202 can communicate with one or more servers 206, one or more external devices such as a controller, actuator, 3D printer, image processor or other such device 204, and a memory storage unit such as, for example, memory or database 208. It should be understood that device 204 may be embodied as a detector device, microcontroller, controller, receiver, transceiver, or other such device.

In the depicted example, external device 204, server 206, and clients 210, 212, and 214 connect to network 202 along with storage unit 208. Clients 210, 212, and 214 may be, for example, personal computers or network computers, handheld devices, mobile devices, tablet devices, smartphones, personal digital assistants, microcontrollers, recording devices, MFDs, etc. Computer system 100 depicted in FIG. 1 can be, for example, a client such as client 210 and/or 212.

Computer system 100 can also be implemented as a server such as server 206, depending upon design considerations. In the depicted example, server 206 provides data such as boot files, operating system images, applications, and application updates to clients 210, 212, and/or 214. Clients 210, 212, and 214 and external device 204 are clients to server 206 in this example. Network data-processing system 200 may include additional servers, clients, and other devices not shown. Specifically, clients may connect to any member of a network of servers, which provide equivalent content.

In the depicted example, network data-processing system 200 is the Internet with network 202 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers consisting of thousands of commercial, government, educational, and other computer systems that route data and messages. Of course, network data-processing system 200 may also be implemented as a number of different types of networks such as, for example, an intranet, a local area network (LAN), or a wide area network (WAN). FIGS. 1 and 2 are intended as examples and not as architectural limitations for different embodiments disclosed herein.

FIG. 3 illustrates a software system 300, which may be employed for directing the operation of the data-processing systems such as computer system 100 depicted in FIG. 1. Software application 305, may be stored in memory 104, on removable storage 112, or on non-removable storage 114 shown in FIG. 1, and generally includes and/or is associated with a kernel or operating system 310 and a shell or interface 315. One or more application programs, such as module(s) or node(s) 125, may be "loaded" (i.e., transferred from removable storage 114 into the memory 104) for execution by the data-processing system 100. The data-processing system 100 can receive user commands and data through user interface 315, which can include input 116 and output 118, accessible by a user 320. These inputs may then be acted upon by the computer system 100 in accordance with instructions from operating system 310 and/or software application 305 and any software module(s) 125 thereof.

Generally, program modules (e.g., module 125) can include, but are not limited to, routines, subroutines, software applications, programs, objects, components, data structures, etc., that perform particular tasks or implement particular abstract data types and instructions. Moreover, those skilled in the art will appreciate that elements of the disclosed methods and systems may be practiced with other computer system configurations such as, for example, handheld devices, mobile phones, smart phones, tablet devices, multi-processor systems, printers, 3D printers, copiers, fax machines, multi-function devices, data networks, microprocessor-based or programmable consumer electronics, networked personal computers, minicomputers, mainframe computers, servers, medical equipment, medical devices, and the like.

Note that the term module or node as utilized herein may refer to a collection of routines and data structures that perform a particular task or implements a particular abstract data type. Modules may be composed of two parts: an interface, which lists the constants, data types, variables, and routines that can be accessed by other modules or routines; and an implementation, which is typically private (accessible only to that module) and which includes source code that actually implements the routines in the module. The term module may also simply refer to an application such as a computer program designed to assist in the performance of a specific task such as word processing, accounting, inventory management, etc., or a hardware component designed to equivalently assist in the performance of a task.

The interface 315 (e.g., a graphical user interface 130) can serve to display results, whereupon a user 320 may supply additional inputs or terminate a particular session. In some embodiments, operating system 310 and GUI 130 can be implemented in the context of a "windows" system. It can be appreciated, of course, that other types of systems are possible. For example, rather than a traditional "windows" system, other operation systems such as, for example, a real time operating system (RTOS) more commonly employed in wireless systems may also be employed with respect to operating system 310 and interface 315. The software application 305 can include, for example, module(s) 125, which can include instructions for carrying out steps or logical operations such as those shown and described herein.

The following description is presented with respect to embodiments of the present invention, which can be embodied in the context of, or require the use of a data-processing system such as computer system 100, in conjunction with program module 125, and data-processing system 200 and network 202 depicted in FIGS. 1-3. The present invention, however, is not limited to any particular application or any particular environment. Instead, those skilled in the art will find that the systems and methods of the present invention may be advantageously applied to a variety of system and application software including database management systems, word processors, and the like. Moreover, the present invention may be embodied on a variety of different platforms including Windows, Macintosh, UNIX, LINUX, Android, Arduino and the like. Therefore, the descriptions of the exemplary embodiments, which follow, are for purposes of illustration and not considered a limitation. In other embodiments, manual control of various aspects may be achievable while closely monitoring readbacks.

The embodiments disclosed herein include a method and system for 3D printing of a custom-fit cast. The disclosed embodiments use a method of obtaining the measurement of an injured limb via X-rays. The patient's X-ray is sent to a specially configured image processing system. The X-ray is analyzed to obtain specific measurements of the patient's anatomy. Next the measurements are converted into instructions that can be used by a material printing machine to produce a custom 3D printed cast, based on the measurements provided within the X-ray.

Figure 4:
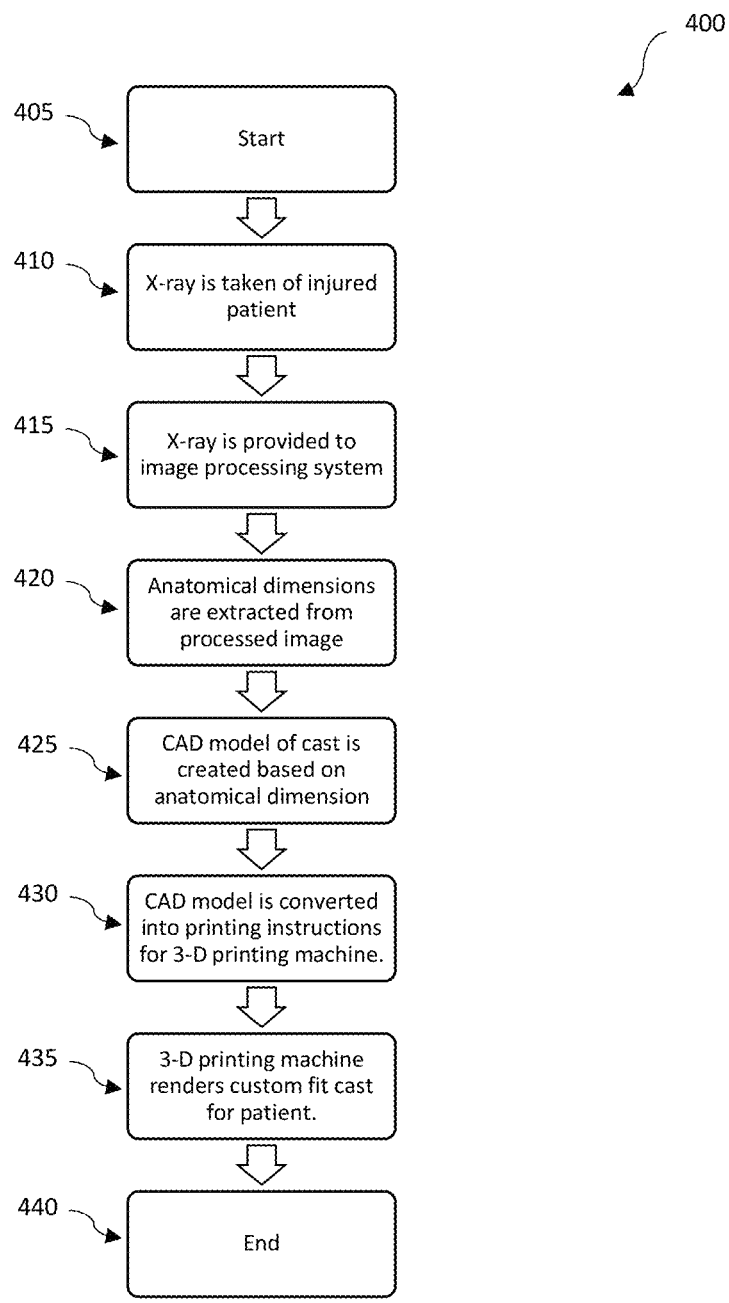
FIG. 4 depicts a method for rendering a cast, in accordance with the disclosed embodiments.

An exemplary method 400 in accordance with the disclosed embodiments is illustrated in the flow chart provided in FIG. 4. The method starts at 405.

At step 410 a medical imaging device can be used to take an image of the patient's injury. Most commonly this step will comprise a garden variety X-ray taken as a standard step in diagnosing an injury. In other embodiments, other medical imaging technology, including but not limited to, radiographic imaging, CT, 3-D tomography, fluoroscopy, Magnetic Resonance Imaging (MRI), Nuclear Magnetic Resonance imaging (NMR), ultrasonic imaging, elastography, or some combination thereof can be used. An important point is that the diagnostic tools used to image the injury can be used, reducing the requirement for secondary or additional imaging to prepare the cast.

The medical image, or X-ray, can next be provided to an image processing system as illustrated at 415. The image processing system can generally comprise a specially configured image processing system, with modules embodied as software. The image processing system can further include an electronic portal that allows the raw image data to be provided to the image processing system.

In an exemplary embodiment, the X-ray image can be provided to the image processing system as a digital imaging and communications in medicine (DICOM) file. DICOM is a medical imaging standard adopted by many healthcare providers. The data file provided to the image processing system 510 can include various attributes, including patient name and other metadata, and image pixel data. The image pixel data is important in the embodiments disclosed, as it is used to determine anatomical lengths as further detailed herein. In certain embodiment the DICOM data file can have one or multiple attributes. Furthermore, a single data file can include a plurality of frames. The DICOM standard can also provide data in 2-D or 3-D.

In certain embodiments, the pixel data associated with an attribute can be compressed when the file size is above a certain threshold. The image processing system can be configured with a receiving portal that can, among other things, be used to decompress the pixel data as necessary for further processing.

Once the image file is uploaded to the image processing system, anatomical dimensions of the injured area can be acquired as illustrated at step 420. In certain embodiments, the image files can be saved and viewed as a DICOM file. The DICOM file includes a defined measurement per pixel. The defined measurement per pixel can be used to determine various dimensions of the anatomy shown in the image file.

For example, in the case of a tibial fracture, a measurement per pixel tool can be used to ascertain the length and diameter of the tibia, fibula, the length and diameter of the foot and foot bones, along with dimensions of soft tissue, skin, or other anatomy associated with the leg. It is important to note that anatomical dimensions of the injury itself, along with the dimensions of the surrounding anatomy can be collected as all of these aspects can be considered in the creation of the custom-fit cast.

In certain embodiments, a DICOM viewer module 535 can be used, which allows a measurement tool to be accessed. The measurement tool can determine the number of pixels associated with a various dimension of the patient anatomy, and then can determine an associated length, width, diameter, circumference, etc., based on the number of pixels and the length per pixel.

Next, at step 425, the physical dimensions of the patient's anatomy can be used to generate a model of a cast. The cast model, can be tailored to the physical dimensions taken from the DICOM file. In certain embodiments, the model can be generated using a CAD program, or other such computer modeling program.

In certain embodiments, a series of template cast forms can be stored as a digital CAD file or other such electronic file, which can later be used as printing instructions for 3-D printers. The series of template cast forms can be selected based on common cast shapes applied by physicians. For example, one template cast form can be for a wrist cast, another can be for a hand cast, another for an arm cast below the elbow, another for an arm cast below the elbow and extending above the elbow, another can be for a lower leg cast, etc.

In certain embodiments, the custom cast forms can further include hinges and clasps, that allow a portion of the cast to be opened, so that the cast can be fitted on a user. The custom fit cast can be printed away from the patient. As such, in order for the cast to be fitted on the patient, the cast must be opened, fitted onto the patient, and then closed and clasped in position on the patient.

The physical dimensions collected from the image in conjunction with the injury itself, can then be used to select the appropriate cast template, and adjust the dimensional characteristics of the cast model to the patient. In this way, the dimensions of the template cast form are readjusted into a custom cast model, specifically tailored to fit the patient based on the dimensional data collected from the DICOM file.

The custom cast model can next be converted into the format required for driving a 3-D printer to render the custom cast as illustrated at 430. In general, this is accomplished with slicing software that prepares the 3D model by deconstructing it into layers. The slicing software can then generate G-code, or other such instructions readable by a 3D printer.

The G-code can then be provided to the 3-D printing machine as shown at step 435, where the 3-D printer renders the custom cast. It should be appreciated that the 3-D printer can comprise any 3-D printing technology including, but not limited to, fused deposition modeling, stereolithography, selective laser sintering, selective laser melting, binder jetting, or other such printing means.

In certain embodiments, some parts of the custom cast can be rendered with one type of material and/or 3D printing process, and other parts of the cast can be printed with another type of material and/or 3D printing process. For example, in some embodiments, the cast can comprise an outer exo-structure formed from plastic fusion deposition modeling or lightweight metal with laser melting technology. An inner surface of the cast can be formed of a softer, custom fit, anti-microbial material. In certain embodiments an antimicrobial spray can be applied to the cast to prevent infection or undesirable smells.

The method for rendering the custom fit cast ends at step 440.

Figure 5A:
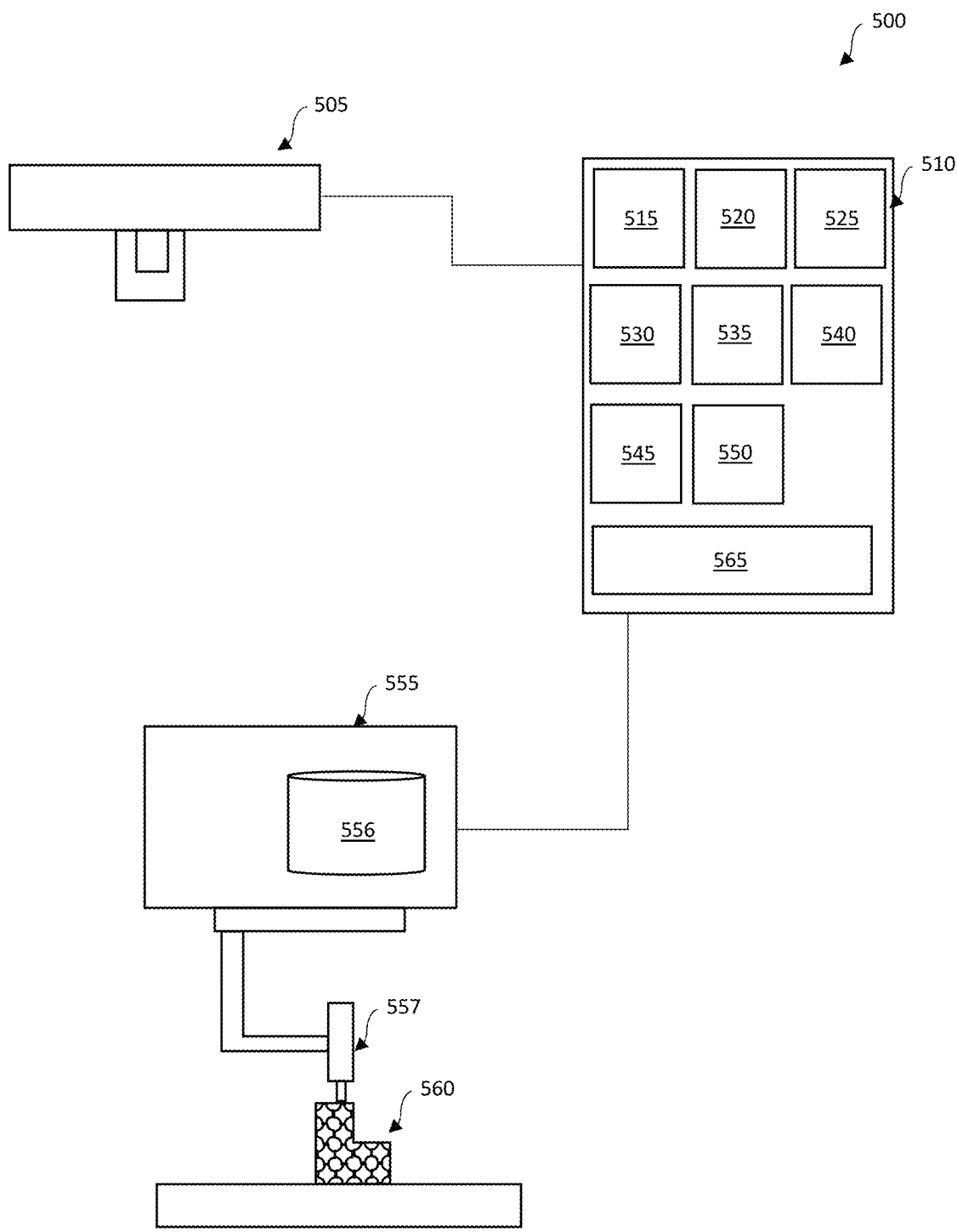
FIG. 5A depicts a system for rendering a cast, in accordance with the disclosed embodiments.
Figure 5B:
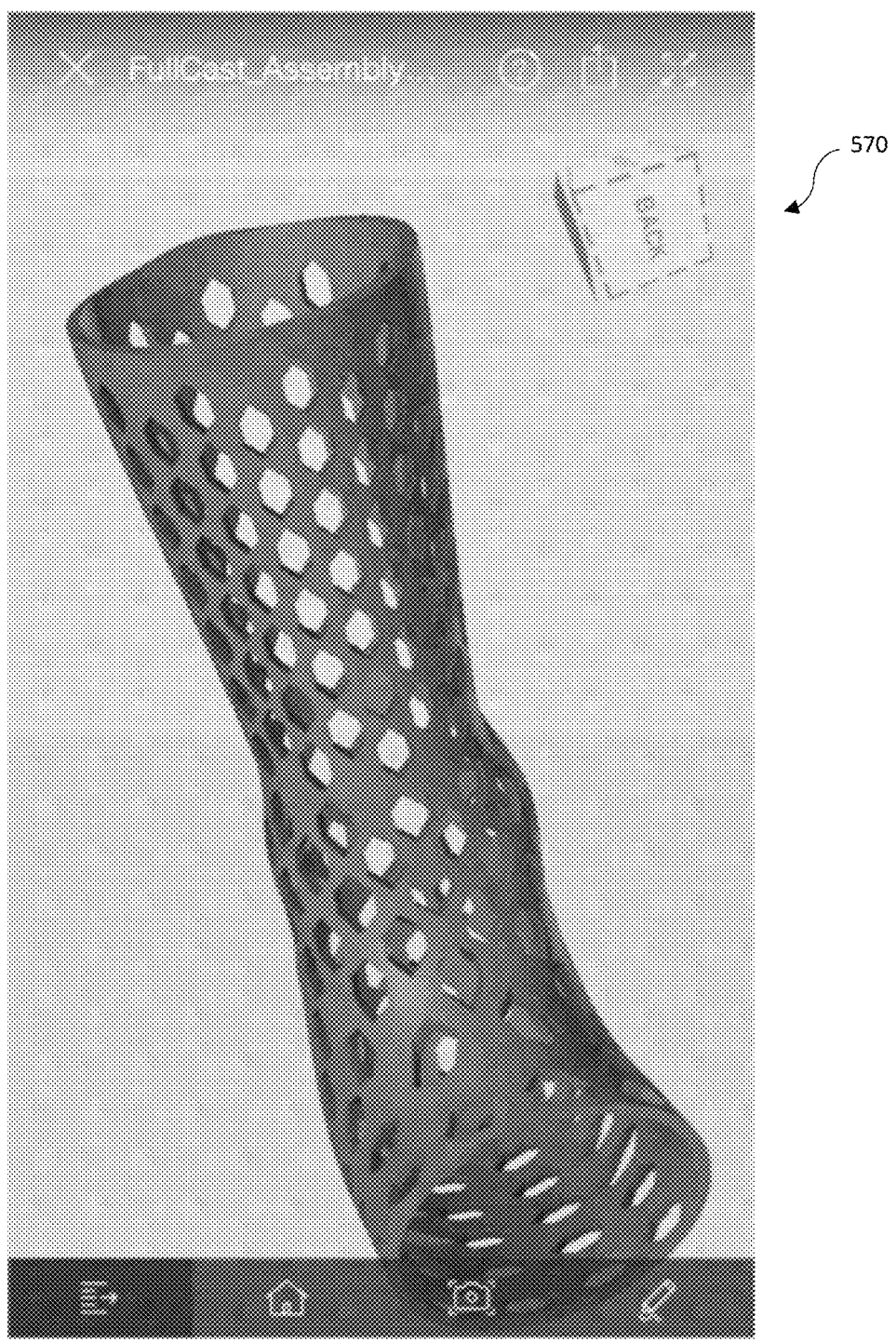
FIG. 5B depicts a screen shot of a software portal for rendering a cast, in accordance with the disclosed embodiments.

FIG. 5 illustrates a block diagram of a cast rendering system 500, which can be used to render a custom-fit cast according to, for example, the method illustrated in FIG. 4.

The system 500 includes an imaging device 505. The imaging device 505 can most commonly comprise an X-ray machine used to take X-rays as part of the standard operating procedure for diagnosis and treatment of an injury. In other embodiments, the imaging device can comprise other medical imaging devices. The use of an X-ray device offers an distinct and important advantage over other devices. Because an X-ray is a standard diagnostic tool for evaluating an injury like a broken bone, in most cases where a broken bone is suspected, an X-ray will be taken. Thus, the patient is relieved of additional effort in securing a second image with a different machine.

The X-ray can be provided to the image processing system or machine 510. In certain embodiments, the image processing machine 510 can comprise a computer and the imaging data can be provided over the internet, via a network connection, as detailed in FIGS. 1-3. The image processing system 510 can include a user portal 515 that comprises a graphical user interface (GUI) that allows the user (e.g. the healthcare provider, patient, etc.) to interact with the image data. The user portal 515 can include an image uploading module 520 where the image data is cataloged in a database and stored for further processing.

Once the image file has been received at the image processing machine 510, initial image processing can be completed with a preprocessing module 525. The initial image processing can include machine learning and/or artificial intelligence configured to identify the injury type and location (e.g. a broken tibia, at the lower end of the tibia). This can also be done manually and/or reviewed by a user, who reviews the image file and uses the user portal 515 to enter the injury type and location.

The preprocessing module 525 can further use artificial intelligence algorithms and/or user input to select a suggested template cast model from a selection of template cast models stored in the image processing machine 510. The template cast model can be selected according to the injury type, location, and other factors used by clinicians. The user can be provided override authority to select a different template cast model if the suggested template cast model is not appropriate for the injury type and location.

A dimension extraction module 530 can be used to extract measurement data associated with the anatomy from the image file provided to image processing machine 510. In certain embodiments, where the image file comprises a DICOM file, a DICOM viewer module 535 associated with the image processing system 510 can be used, which allows a measurement tool to be accessed. The measurement tool can determine the number of pixels associated with a various dimension of the patient anatomy, and then can determine an associated length, width, diameter, circumference, etc., based on the number of pixels and the length per pixel. This process can be applied to various anatomical features illustrated in the DICOM image, and can include measurements from multiple parts of the image. For example, the dimensions of the affected anatomy can be collected, as well as dimensions associated with the injury, and relative location of the injury to other anatomical features.

The extracted dimensional characteristics of the anatomical features in the image file can be sorted and transmitted to a modeling module 540. In certain embodiments the modeling module 540 can comprise a 3D modeling system such as a solid modeling computer-aided design system (CAD) or a computer-aided engineering system (CAE). The measurements taken at specific locations in the X-ray can be uploaded into a table built into the CAD or CAE system.

A method for constructing a table with the modeling module 540 can be used. First a line can be sketched around aspects in the image to form the superior structure outline (e.g., the anterior/posterior side of a forearm). In certain embodiments, this can be done automatically, or can be completed by a person using tools provided by the image processing system 510. Multiple points can be added in the line to reference the measurement coordinates.

Each point is measured from its coordinate point to an origin point, to obtain the width of the point (thereby defining the width of the measurement). In certain embodiments a side box can be displayed in the GUI, displaying a measurement. This defines the depth of the point, from the origin to the outside point.

The point is then measured from the coordinate point to the origin point to obtain the length of the point (defining the length of the measurement). A side box tool can display the measurement. Both the length and width (e.g. anterior/posterior and lateral) measurements are defined. The measurement boxes can be modified/named and associated with the point in reference, for example "AP_Height". After exiting the "sketch', a silver displayed shape is shown. The dimensions can be named for the columns in the table—for example, selecting "AP_Height1" can display that dimensional point on the table.

Once the dimension is named on the table, a new patient row can be created, new measurements can be entered in the respective spots, and a computer aided drafting program can redesign the cast shape to correlate to the measurements.

Within the DICOM viewer there is a measurement tab that can be utilized as a measuring ruler. Clicking on the ruler and two points will result in the measurement of the associated dimension, for example, a line from point A to B is placed on a patient X-ray. The measurement can be converted from mm to inches. The template can similarly be converted into any unit of measurement (mm, inches, cm, feet, etc.).

With the new measurements obtained, they can be entered into the table under the respective anatomical designation. A spreadsheet cell (e.g. "wrist to middle palm") for the patient ("Patient Doe") in the newly created patient row can be populated. The tables can be built in a spreadsheet program such as Microsoft Excel® or other such spreadsheet system.

The dimensional information gathering step can recycle or iterate until all points on the table have designated dimensions. The CAD program saves the new design table as a model under the design table tab for the patient name. Clicking on the patient name (ex. "Patient Doe") can initiate reformatting and scaling, and the model can be updated to the new dimensions entered within the table. The template at this point is specifically assigned to the patient and the pattern is scaled within the CAD (e.g. Solidworks®) program. The new patient template is then ready to print.

Once the correct cast template model has been selected and the measurement data has been stripped from the image and provided to the modeling module 540, cast design module 545 can adjust the dimensions of the cast template model according to the measurement data. Such adjustments can be made in consideration of the location of the injury, the dimensions of the skeletal structures, the dimensions of the soft tissue surrounding the injured area, and the dimensions of the outer anatomic features.

A cast customization module 550 can provide an interface where a user can select additional customizations for the cast before it is rendered. Such customizations can include, material selections, which can include multiple materials which may be used in different areas of the cast. For example, a soft anti-microbial material can be used on the interior surfaces of the cast to prevent skin irritation, a lightweight structure can be used for the exo-structure of the cast, and a gripping material can be deposited on portions of the exterior of the cast where non-slip functionality is desired (e.g. the bottom surface of a cast covering the foot).

In certain embodiments, the cast customization module 550 can use preferences learned from a given health care provider's historical selections to provide optional customization filters. For example, an orthopedist may prefer placement of the cast in a specific way, despite the imaging data. This could include, for example, a cast that is c-shaped and "cupped" to position the patient's hand in a way to hold objects. Such adjustments can be immediately built into the new cast according to the health care provider recommendation rather than requiring additional X-rays.

The cast customization module 550 can further include a patient portal that allows the patient to select various cosmetic customizations for the cast. Such customizations can include, cast color which can further include multiple colors, design features in the cast such as cosmetic designs (e.g. an American flag design, the patients name) in the cast, integrated structural characteristics such as the patient's name in the structure of the cast, or other such structural designs. Certain surfaces on the cast can be made flat or smooth, so that the cast can be written on by a patient's friends and family.

The cast customization module 550 can provide an output that allows the health care provider and/or the patient to visualize the customizations. A screen shot 570 is provided in FIG. 3B illustrating such an interface 565 associated with the image processing machine 510. When those customizations are finalized, the customizations are incorporated into the CAD or CAE model and converted into a G-code file with a slicer, or other such file that can be read by a 3D printing device 555.

The G-code file can be sent to the 3D printing device 555 where the cast can be rendered. The 3D printing device 555 can comprise one or more of an additive manufacturing machine that can be configured to print multiple materials, an SLS machine, which can use nylon fiber, a PLA machine where the PLA machine can also have carbon fiber weaved into the printing material, and can provide high heat tolerance.

In the exemplary embodiment illustrated in FIG. 5A the printing device 555 comprises a fused deposition modeling device with a filament roll 556. Filament from the filament roll 556 is provided to printing head 557. The printing head 557 is dynamically adjusted as heated filament is extruded to produce the desired structure 560. It should be appreciated that this type of 3D printing is exemplary and other printing methods can alternatively, or additionally, be used in accordance with the disclosed embodiments.

Figure 6A:
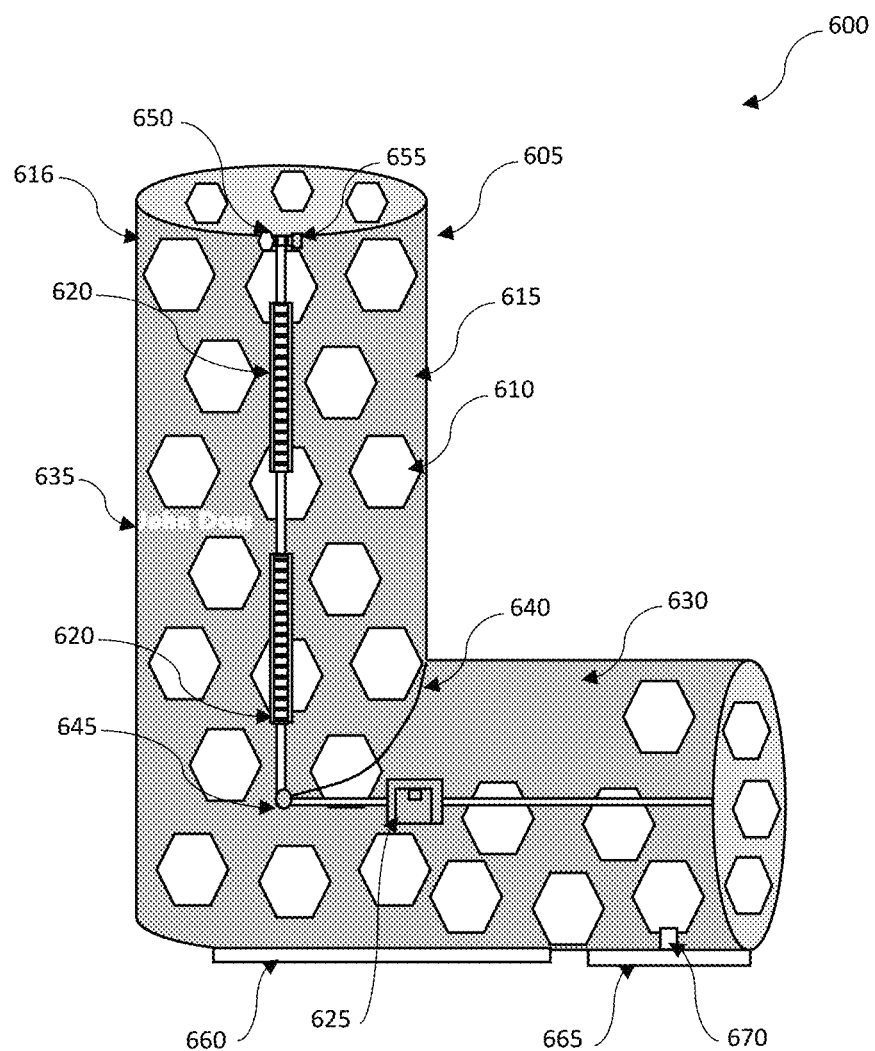
FIG. 6A depicts a cast rendered in accordance with the methods and systems disclosed herein in accordance with an embodiment.
Figure 6B:
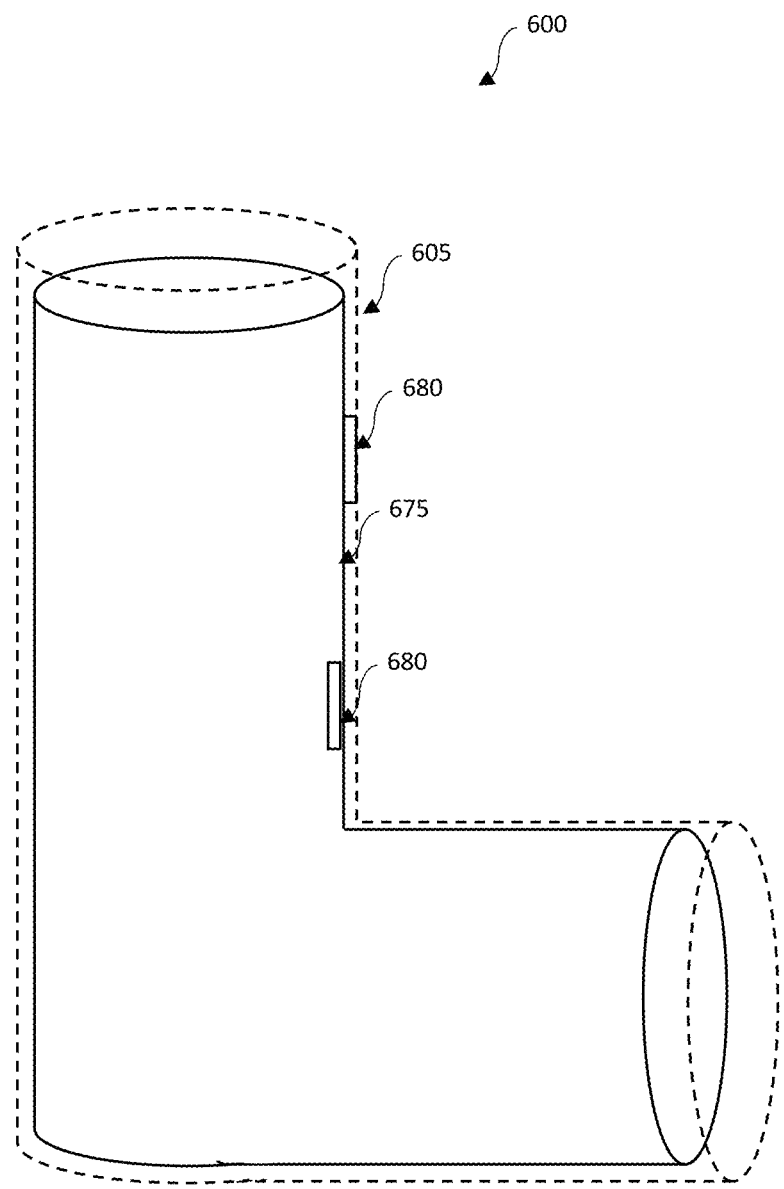
FIG. 6B depicts a cast rendered in accordance with the methods and systems disclosed herein in accordance with an embodiment.

FIGS. 6A-6B illustrate an exemplary cast 600 that can be produced in accordance with the methods and systems disclosed herein. The exemplary cast 600 is shown as a leg cast but it should be appreciated that in other embodiments, some or all of the features illustrated in FIGS. 6A-6B can be used in association with casts configured for other parts of the human body, or for other animals. It should further be understood that various aspects of the cast 600 may not be included in a cast 600. Thus, various optional features of the casting system are illustrated in the exemplary embodiment of a cast 600 in FIG. 6A-6B, with the understanding that the cast 600 can incorporate any or all of such features. It should further be understood that any of the features related to cast 600 can be produced using the system 500 and method 400 disclosed herein.

The cast 600 can be formed with an exo-structure 605. In certain embodiments, the exo-structure 605 can be formed of plastic, polymer, rubber, metal or some combination thereof. The exo-structure 605 can be formed as a plurality of honeycombed shaped hexagons 610 printed into a structure that is both lightweight and strong. In other embodiments other patterns for the structure can be used, such as a bone shaped pattern, circles, semi-circles, triangles, etc. The exo-structure 605 can be rendered with carbon fiber weaved into the exo-structure 605.

The cast 600 can additionally be printed as multiple pieces such as a first half 615 and a second half 616. The halves can be printed independently, making it easy for the cast 600 to be fitted on the patient. The cast halves can be joined with joints 620 which can comprise hinges, that connect the halves (such as first half 615 and second half 616). The cast 600 can be secured in place with fasteners 625, which can comprise clasps, clips, screws, rivets or the like. The fastener 625 can be printed on the exo-structure 605. In certain embodiments, the fastener 625 can further be configured to allow the tightness of the cast to be adjusted to be tighter or looser. In such cases the fastener 625 can comprise a clasp with a bar formed on one half 615 of the cast that is configured to engage a plurality of spaced ridges formed on the opposing half of the cast 616. It should be appreciated that in other embodiments, the exo-structure 605 can be printed in more than two pieces, and multiple joints and fasteners can be used to connect the various pieces.

The exo-structure 605 of the cast 600 can further be configured with a locking screw 650 to secure the first half 615 and second half 616 together. In certain embodiments, this can comprise a screw mount 655 along a joint 620 between the first half 615 and second half 616 of the cast 600. The locking screw can be secured in place to make it more difficult to remove the cast 600.

Cosmetic features can be incorporated on the exo-structure 605. For example, a portion of the exo-structure 605 can be printed with a smooth surface 630 receptive to marker or ink, so that friends and family of the patient can sign the outer surface of the exo-structure 605. The exo-structure 605 can further be rendered with design elements 635 according to patient selections. For example, the design element 635 could include a name, phrase, slogan, design, image, or other such cosmetic element. The exo-structure 605 can also be printed using filament of different colors to achieve various cosmetically desired effects.

Because the cast 600 is custom sized to the patient, and because the casting material of the exo-structure 605 has a high strength to weight ratio, the profile of the cast 600 can be much thinner than traditional casts. As such, the cast 600 profile can allow pants or shirts to be worn over the cast 600. Similarly, a sock can fit over the cast 600.

The cast 600 can further include a joint 640 configured with a pivot 645 that allows the attitude of one section of the cast 600, to be adjusted with respect to the other section of the cast 600. The adjustable angle between sections of the cast 600, allows a healthcare provider to change the angle of one bone with respect to another bone, as time progresses, to facilitate better healing. For example, as a bone heals, the health care professional may wish to adjust the angle of the connecting bone from 90 degrees, to 45 degrees to facilitate healing and joint health.

A non-slip material 660 can be printed on the exterior of the exo-structure 605. The non-slip material 660 can be strategically printed on portions of the exo-structure 605 where it might be desirable to prevent slipping, such as the bottom of the foot for a foot or leg cast. In addition, a removable cast shoe 665 comprising a protective and/or non-slip surface can be removably connected to a portion of the exo-structure 605 with a clip 670. The cast shoe 665 is configured to prevent contamination or soiling of the exo-structure 605 (e.g. if the patient is walking on a portion of the cast) and/or to provide an additional non-slip surface, on a portion of the exo-structure 605.

FIG. 6B illustrates an interior structure 675 associated with a cast 600. The interior structure 675 can comprise an antimicrobial material that is printed (or otherwise disposed) on the interior surface of the exo-structure 605. The interior structure 675 can be formed of a softer material including fiber, soft rubber, plastic, etc. that is comfortable against the patient's skin. Spacer 680 can be formed inside the interior structure 675 or between the interior structure 675 and the exo-structure 605 to adjust the fit of the cast as the muscles atrophy. The spacers 680 can be custom sized according to the same methods illustrated above to fit the anatomy of the patient. The spacers 680 can include multiple spacers 680 of multiple shapes disposed in various positions in the cast 600. The spacer 680 can also be used in association with the tightening fasteners 625 to adjust the fit of the cast 600.

Figure 7:
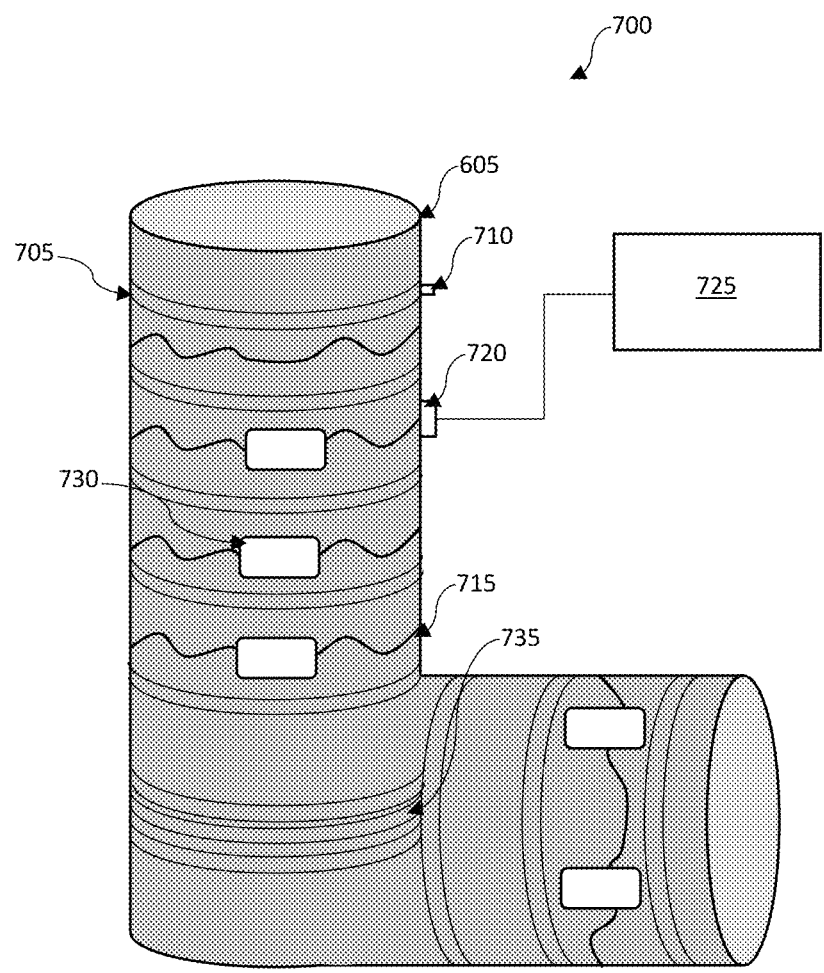
FIG. 7 depicts another embodiment of a cast, in accordance with the disclosed embodiments.
Figure 8:
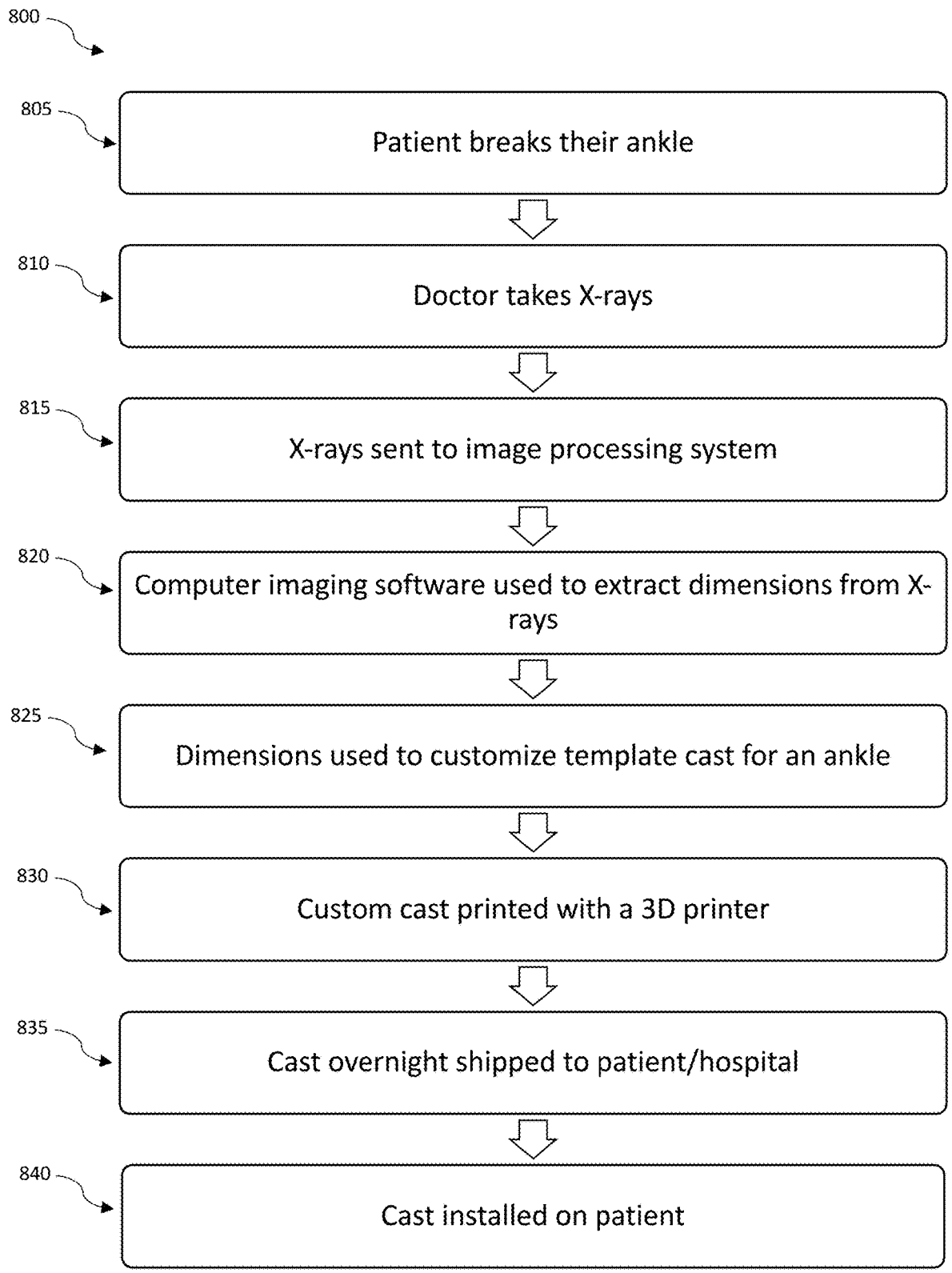
FIG. 8 depicts a workflow for rendering a 3D printed a cast in accordance with the disclosed embodiments.

FIG. 7 illustrates another embodiment of a cast 700 rendered according to the systems and methods disclosed herein. In this embodiment, the cast 700 can include any of the features of cast 600 along with therapeutic modifications.

For example, the cast 700 can be rendered where the exo-structure 605 or the inner structure 675 can be formed as fluidic channels 705, or micro-fluidic channels. The fluidic channels 705 can include a fluid port 710 that allows hot or cold liquid to be inserted into the structure of the exo-structure 605 or the inner structure 675. The port 710 can comprise a valve such as a check valve that allows fluid to enter the fluidic channels 705. The fluid can be used to control the temperature of the tissue surrounded by the cast 700 as may be necessary to reduce or prevent inflammation or for other such therapeutic reasons.

The inclusion of fluidic channels 705 and port 710 can be selected by the health care professional or patient as a design option for the cast using the cast customization module 550, and can be rendered as a part of the cast 700. In certain embodiments, a concentration of fluidic channels 735 can surround the area of the anatomy where the injury is present, or at some other desired location, to provide localized temperature control. This location can be selected by the health care professional or patient as a design option for the cast 700 using the cast customization module 550.

The cast 700 can further include conducting wire 715 attached to one or more electrodes 730 disposed in the exo-structure 605 or the interior structure 675, wherein the conducting wire 715 is configured to send electrical pulses to the electrode. The system can include an interface 720 that allows the conducting wire 715 to be electrically connected to an electric stimulation unit 725 comprising an electric stimulation (E-STIM) or transcutaneous electrical nerve stimulation (TENS) unit. The electric stimulation unit 725 can be used to send electric pulses to the electrodes 730 which in turn provide electric stimulation therapy.

The disclosed embodiments provide a modern cast, which is lighter, more comfortable, waterproof and more hygienic, offering a superior casting product to those currently available.

In the exemplary embodiment disclosed herein an X-ray file(s) of a patient's injured member is transmitted to an electronic portal or digital system as a DICOM file. DICOM files have a defined measurement per pixel. The patients X-ray can then be viewed using a DICOM viewer, which allows a measurement tool to be accessed. The measurements at specific places on the X-ray are obtained and can be uploaded into a table built into a design program such as SolidWorks®. In certain embodiments, software can enter the data from the measurements into the table. The table is then used by the design program to scale a predesigned cast template to new measurements corresponding to the patient. The new design is then exported as a CAD file/.stl data and sent to an additive manufacturing printer (e.g. SD printer) to be printed and built.

In this way, the embodiments herein produce patient specific, additive manufactured orthopedic immobilization devices, to change the current casting device methods and market. The orthopedic casts, which are designed specifically for the patient and can be built quickly. In certain embodiments the cast can be built remotely from the health care provider and patient and shipped throughout the United States.

The embodiments can use X-rays taken in the normal course of diagnosis or treatment sent by the hospital or clinic, to build a cast from the dimensions provided on the DICOM radiology file.

The following exemplary situation is meant to Illustrate additional advantages of the embodiments disclosed herein. At step 805 of method 800 a patient in New York slips and falls, breaking their ankle. The hospital and/or doctor in charge of caring for the patient takes an AP and lateral view X-ray at step 810 and sends them to an image processing system at step 815, located, for example, in New Mexico, via a secure internet connection. Computer imaging software gathers the dimensions at step 820, incorporates them into a CAD design at step 825, and the cast is printed with a 3-D printer at step 830. At step 835 the cast is then sent overnight to the doctor/hospital of the patient's choice, where it can be applied at step 840, in less than 48 hours from the time it was sent to the image processing system. This dramatically decreases production time and patient inconvenience.

The disclosed embodiments of the custom fit immobilization device can be built from high temperature resistant plastic. It can therefore be waterproof while maintaining structural rigidity in heat or other inclement weather conditions. The design of the disclosed cast is intended provide as much skin exposure as possible. The open-air concept prevents infections and allows easier access to areas of discomfort. The inner portion of the cast that touches the skin can printed with a more comfortable material, such as, for example, a rubberized material, preventing the potential for irritation caused by the rigid material. The cast can be built with a plastic filament, so that it can be washed while on the patient. The disclosed embodiments thus provide a hygienic and more comfortable immobilization device that provides a more rigid support than current cast products.

Based on the foregoing, it can be appreciated that a number of embodiments, preferred and alternative, are disclosed herein. It should be appreciated that variations of the above-disclosed and other features and functions, or alternatives thereof, may be desirably combined into many other different systems or applications. In an embodiment, a method comprises obtaining at least one measurements taken from at least one image of a body part, selecting a template cast model, modifying the template cast according to the measurements taken from the at least one image to generate a custom cast model, and rendering a custom cast based on the custom cast model. The at least one image can comprise an X-ray.

In an embodiment, the method further comprises customizing design features of the custom cast in a user portal.

In an embodiment, the method further comprises rendering a first portion of the custom cast, rendering a second portion of the custom cast, and rendering a fastener for connecting the first portion of the custom cast to the second portion of the custom cast. In an embodiment, rendering a custom cast further comprises printing the custom cast with a 3D printer.

In an embodiment, the method further comprises printing an exo-structure of the custom cast and printing an interior structure of the custom cast. In an embodiment, the method further comprises printing the exo-structure with a rigid material and printing the interior structure with an anti-microbial material.

In an embodiment a method for rendering an orthopedic immobilization device comprises receiving at least one X-ray at an image processing system, extracting dimensions of at least one anatomical structure in the X-ray, generating a custom cast model according to the dimensions taken from the at least X-ray, and rendering a custom cast based on the custom cast model.

In an embodiment, receiving the at least one X-ray at the image processing system further comprises receiving the X-ray as a digital imaging and communications in medicine (DICOM) file. In an embodiment, extracting dimensions of at least one anatomical structure in the X-ray further comprises determining a number of pixels that defines the at least one anatomical structure, reading the length per pixel value associated with the DICOM file, and assigning the dimension of the at least one anatomical structure according to the length per pixel value associated with the DICOM file and the number of pixels that defines the at least one anatomical structure.

In an embodiment, rendering a custom cast further comprises printing the custom cast with a 3D printer.

In an embodiment, the method further comprises providing a user portal, the user portal being configured to allow a user to select at least one customization of the custom cast.

In an embodiment, the method further comprises extracting dimensions of at least one injured anatomical feature in said X-ray. In an embodiment, the method further comprises customizing the custom cast according to the dimensions of the at least one injured anatomical feature.

In an embodiment, the method further comprises incorporating a fluidic channel in the custom cast. In an embodiment, the method further comprises incorporating at least one conducting wire and at least one electrode in the custom cast.

In yet another embodiment, a system comprises an imaging device configured to take at least one image of at least one anatomical structure, an image processing system comprising at least one processor and a storage device communicatively coupled to the at least one processor, the storage device storing instructions which, when executed by the at least one processor, cause the at least one processor to perform operations comprising: extracting dimensions of the at least one anatomical structure in the at least one image taken by the imaging device, selecting a template cast model, and modifying the template cast model according to the measurements taken from the at least one image to generate a custom cast model, and a 3D printing device configured to render a custom cast according to the custom cast model.

In an embodiment the imaging device comprises an X-ray. In an embodiment the X-ray is provided to the at least one image processing system as a DICOM file. In an embodiment the image processing system is further configured to perform operations comprising determining a number of pixels that defines the at least one anatomical structure, reading the length per pixel value associated with the DICOM file and assigning the dimension of the at least one anatomical structure according to the length per pixel value associated with the DICOM file and the number of pixels that defines the at least one anatomical structure.

It should be understood that various presently unforeseen or unanticipated alternatives, modifications, variations or improvements therein may be subsequently made by those skilled in the art which are also intended to be encompassed by the following claims.

What is claimed is:

1. A method comprising:
    obtaining measurements taken from a plurality of images of a body part, the measurements comprising a length and a diameter of a bone associated with the body part, a length and diameter of soft tissue associated with the body part, and dimensions of outer anatomical features associated with the body part;
    selecting a template cast model from a plurality of template cast models, each of the plurality of template cast models being configured for a different anatomical feature and injury type;
    modifying the template cast according to the measurements taken from the plurality of images to generate a custom cast model; and
    rendering a custom cast based on the custom cast model by printing an exo-structure of the custom cast and providing an interior structure of the custom cast, wherein the exo-structure comprises a plurality of honeycomb hexagons;
    wherein rendering the custom cast further comprises:
    rendering a first portion of the custom cast;
    rendering a second portion of the custom cast; and
    rendering a fastener for connecting the first portion of the custom cast to the second portion of the custom cast.

2. The method of claim 1 wherein the plurality of images comprises an X-ray.

3. The method of claim 1 further comprising:
    customizing design features of the custom cast in a user portal, the design features comprising:
    materials of the custom cast;
    colors of the custom cast;
    cosmetic designs on the custom cast;
    flattened surfaces on the custom cast configured to accept writing; and
    shape of the custom cast.

4. The method of claim 1 further comprising:
    providing optional cast customization filters for cast customization based on use preferences from a health care provider's historical cast customization selections.

5. The method of claim 3 wherein rendering a custom cast further comprises:
    providing a digital visualization of the custom cast on a computer; and
    printing the custom cast with a 3D printer.

6. The method of claim 1 further comprising:
    printing the exo-structure with a rigid material; and
    wherein the interior structure comprises an anti-microbial material.

7. A method for rendering an orthopedic immobilization device comprising:
    receiving at least one X-ray at an image processing system;
    extracting dimensions of at least one anatomical structure in the at least one X-ray the dimensions comprising dimensions of a bone associated with the at least one anatomical structure, dimensions of soft tissue associated with the at least one anatomical structure, and dimensions of the outer anatomical features associated with the anatomical structure;
    determining a body part of the anatomical structure from the at least one X-ray;
    generating a custom cast model according to the dimensions taken from the at least one X-ray; and
    rendering a custom cast based on the custom cast model, the custom cast comprising an exo-structure of the custom cast and an interior structure of the custom cast, wherein the exo-structure comprises a plurality of honeycomb hexagons;
    wherein the custom cast further comprising: a first portion of the custom cast, a second portion of the custom cast, and a fastener for connecting the first portion of the custom cast to the second portion of the custom cast.

8. The method for rendering an orthopedic immobilization device of claim 7 wherein receiving the at least one X-ray at the image processing system further comprises:
    receiving the at least one X-ray as a digital imaging and communications in medicine (DICOM) file.

9. The method for rendering an orthopedic immobilization device of claim 8 wherein extracting dimensions of the at least one anatomical structure in the at least one X-ray further comprises:
    determining a number of pixels that defines the at least one anatomical structure;
    reading a length per pixel value associated with the DICOM file; and
    assigning the dimensions of the at least one anatomical structure according to the length per pixel value associated with the DICOM file and the number of pixels that defines the at least one anatomical structure.

10. The method for rendering an orthopedic immobilization device of claim 7 wherein rendering a custom cast further comprises:
    printing the custom cast with a 3D printer.

11. The method for rendering an orthopedic immobilization device of claim 8 further comprising:
    providing a user portal, the user portal being configured to allow a user to select at least one customization of the custom cast, the at least one customization comprising:
    materials of the custom cast;
    colors of the custom cast;
    cosmetic designs on the custom cast;
    flattened surfaces on the custom cast configured to accept writing; and
    shape of the custom cast.

12. The method for rendering an orthopedic immobilization device of claim 7 further comprising:
    extracting dimensions of at least one injured anatomical feature in the at least one X-ray.

13. The method for rendering an orthopedic immobilization device of claim 12 further comprising:
    customizing the custom cast according to the dimensions of the at least one injured anatomical feature.

14. The method for rendering an orthopedic immobilization device of claim 7 further comprising:
    incorporating a fluidic channel in the custom cast configured to accept hot or cold liquid flow in the custom cast.

15. The method for rendering an orthopedic immobilization device of claim 7 further comprising:
    incorporating at least one conducting wire and at least one electrode in the custom cast.

* * * * *